(12) United States Patent
Mori et al.

(10) Patent No.: US 7,553,974 B2
(45) Date of Patent: Jun. 30, 2009

(54) CRYSTAL OF (2R,4R)-MONATIN POTASSIUM SALT AND SWEETENER COMPOSITION CONTAINING SAME

(75) Inventors: Ken-ichi Mori, Kawasaki (JP); Eriko Ono, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 587 days.

(21) Appl. No.: 11/180,622

(22) Filed: Jul. 14, 2005

(65) Prior Publication Data
US 2006/0014819 A1 Jan. 19, 2006

(30) Foreign Application Priority Data
Jul. 14, 2004 (JP) .............................. 2004-207680

(51) Int. Cl.
*A61K 31/405* (2006.01)
*C07D 209/18* (2006.01)
(52) U.S. Cl. ..................... 548/195; 514/419; 426/548
(58) Field of Classification Search ............... 546/495; 426/548; 514/419
See application file for complete search history.

(56) References Cited

U.S. PATENT DOCUMENTS

| | | | | |
|---|---|---|---|---|
| 4,975,298 A | * | 12/1990 | Van Wyk et al. | 426/548 |
| 5,128,164 A | * | 7/1992 | Van Wyk et al. | 426/548 |
| 5,994,559 A | | 11/1999 | Abushanab et al. | |
| 6,761,922 B2 | * | 7/2004 | Ishii | 426/548 |
| 2005/0004394 A1 | | 1/2005 | Kawahara et al. | |
| 2005/0020508 A1 | | 1/2005 | Amino et al. | |
| 2006/0014819 A1 | | 1/2006 | Mori et al. | |

FOREIGN PATENT DOCUMENTS

| | | |
|---|---|---|
| WO | 03/045914 | 6/2003 |
| WO | WO2005/082850 * | 9/2005 |
| ZA | 87 4288 | 6/1987 |
| ZA | 88 4220 | 6/1988 |

OTHER PUBLICATIONS

Muzaffar et al. "Polymorphism and drug availability" J. Phar. 1(1) 59-66 (1979).*
Jain et al. "Polymorphisom in pharmacey" Indian Drugs 23(g)315-329 (1986).*
Doelker et al. "Crystalline modification . . . " CA 138:209993 (2002).*
Doelker et al."Physicochemical behavior or active . . . " CA 132:325872 (2000).*
Otsuka et al. "effect of polymorphic . . . " Chem. Pharm. Bull, 47(6) 852-856 (1999).*
Ulrich "Crystallization" Kirk-Othmer encyclopedia of chem. tech. p. 95-147 (2002).*
Berstain "polymorphism in molecular crystals" p. 118, 272 (2002).*
Davidovich et al. "detection of polymorphsm . . . " Am. Pharm. Rev. v. 7(1) p. 10, 12, 14, 16, 100 (2004).*
Seddon "Pseudopolymorph . . . " Crystal growth & Design 4(6) p. 1087 (2004) (Web print out 2 pages).*
Exhibit I.*
Mori et al. "Process for producing monatin . . . " CA143:266817 (2005).*
U.S. Appl. No. 11/180,622, filed Jul. 14, 2005, Mori, et al.
U.S. Appl. No. 10/860,018, filed Jun. 4, 2004, Amino et al.
U.S. Appl. No. 11/249,629, filed Oct. 14, 2005, Mori.
U.S. Appl. No. 11/180,622, filed Jul. 14, 2005, Mori et al.
K. Nakamura et al, "Total Synthesis of Monatin", *Organic Letters*, vol. 2, No. 19, 2000, pp. 2967-2970.
C. Holzapfel et al, "A Simple Cycloaddition Approach to a Racemate of the Natural Sweetener Monatin", *Synthetic Communications*, vol. 24, No. 22, 1994, pp. 3197-3211.
R. Vleggaar et al, "Structure Elucidation of Monatin, a High-intensity Sweetener Isolated from the Plant *Schlerochiton ilicifolius*," *J. Chem. Soc. Perkin Trans.1*, 1992, pp. 3095-3098.
U.S. Appl. No. 11/406,262, filed Apr. 19, 2006, Mori.

* cited by examiner

*Primary Examiner*—Celia Chang
(74) *Attorney, Agent, or Firm*—Oblon, Spivak, McClelland, Maier & Neustadt, P.C.

(57) ABSTRACT

Crystals of (2R,4R)-monatin potassium salt which exhibit an X-ray powder diffraction pattern having characteristic peaks at diffraction angles 2θ of 5.5°, 7.2°, 8.1°, 8.9°, and 16.3°, by powder X-ray diffraction (Cu—Kα radiation), are superior in sweetness, preservation stability, solubility, and color stability.

20 Claims, 13 Drawing Sheets

US 7,553,974 B2

CRYSTAL OF (2R,4R)-MONATIN POTASSIUM SALT AND SWEETENER COMPOSITION CONTAINING SAME

CROSS REFERENCES TO RELATED APPLICATIONS

This application claims priority to Japanese Patent Application No. 2004-207680, filed on Jul. 14, 2004, which is incorporated herein by reference in its entirety.

BACKGROUND OF THE INVENTION

1. Field of the Invention

The present invention relates to crystals of (2R,4R)-monatin potassium salt having a superior sweetness.

2. Discussion of the Background

Monatin is a natural amino acid derivative isolated from the root bark of a native plant (*Schlerochiton ilicifolius*) of northern Transvaal of South Africa, and its structure has been reported by R. Vleggaar et al to be (2S,4S)-2-amino-4-carboxy-4-hydroxy-5-(3-indolyl)-pentanoic acid ((2S,4S)-4-hydroxy-4-(3-indolylmethyl)-glutamic acid) (R. Vleggaar et al., *J. Chem. Soc. Perkin Trans.*, pp. 3095-3098, (1992)). The synthesis of monatin is described in, for example, ZA 88/4220; U.S. Pat. No. 5,994,559; WO03/045914; C. W. Holzapfel et al., *Synthetic Communications*, 24(22), pp. 3197-3211 (1994); K. Nakamura et al., *Organic Letters*, 2, pp. 2967-2970 (2000); and the like.

Moreover, in WO03/045914, crystals of the stereoisomer ((2S, 4R) form, the (2R,4R) form, and the (2R,4S) form) of monatin were isolated. It has been disclosed that, of these, the (2R,4R) form of monatin (hereinafter sometimes to be abbreviated as (2R,4R)-monatin) shows high sweetness, and particularly, a crystal of the (2R,4R)-monatin potassium salt is also superior in regard to preservation stability and the like. The crystal of the monatin potassium salt concretely disclosed in WO03/045914 is a crystal of a monopotassium salt, and the crystal shows an X-ray diffraction pattern having characteristic peaks at diffraction angles 2θ of 6.1E, 12.2E, 18.3E, 20.6E, and 24.5E by powder X-ray diffraction (Cu—Kα radiation).

While the above-mentioned salt has superior characteristics in regard to preservation stability and the like as mentioned above, a salt having improved solubility and color stability would be more preferable.

SUMMARY OF THE INVENTION

Accordingly, it is one object of the present invention to provide novel crystals of a salt of (2R,4R)-monatin having a superior sweetness, and which is superior in regard to preservation stability, solubility, and color stability.

It is another object of the present invention to provide a method of making such crystals.

These and other objects, which will become apparent during the following detailed description, have been achieved by the inventors' discovery that a potassium salt of (2R,4R)-monatin having a particular powder X-ray diffraction spectrum, which (2R,4R)-monatin having a sweetness highest of the four kinds of stereoisomers of monatin, is superior in regard to preservation stability, as well as solubility and color stability.

Accordingly, the present invention provides:

(1) a crystal of (2R,4R)-monatin potassium salt which exhibits an X-ray powder diffraction pattern having characteristic peaks at diffraction angles 2θ of 5.5°, 7.2°, 8.1°, 8.9°, and 16.3°, by powder X-ray diffraction using Cu—Kα radiation.

(2) a crystal of (2R,4R)-monatin potassium salt having a molar ratio of potassium to (2R,4R)-monatin within the range of 1.2 to 2.

(3) the crystal of (1), wherein the molar ratio of potassium to (2R,4R)-monatin is within the range of 1.2 to 2.

(4) the crystal of any of (1) to (3), wherein the molar ratio of water to (2R,4R)-monatin is within the range of 0.9 to 1.7.

(5) a sweetener composition comprising the crystal of any of (1) to (4), and the like.

According to the present invention, a crystal of (2R,4R)-monatin potassium salt, which shows a preservation stability of the same level as the crystal of the (2R,4R)-monatin monopotassium salt, and a solubility and color stability superior to those of the monopotassium salt crystal, can be provided.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
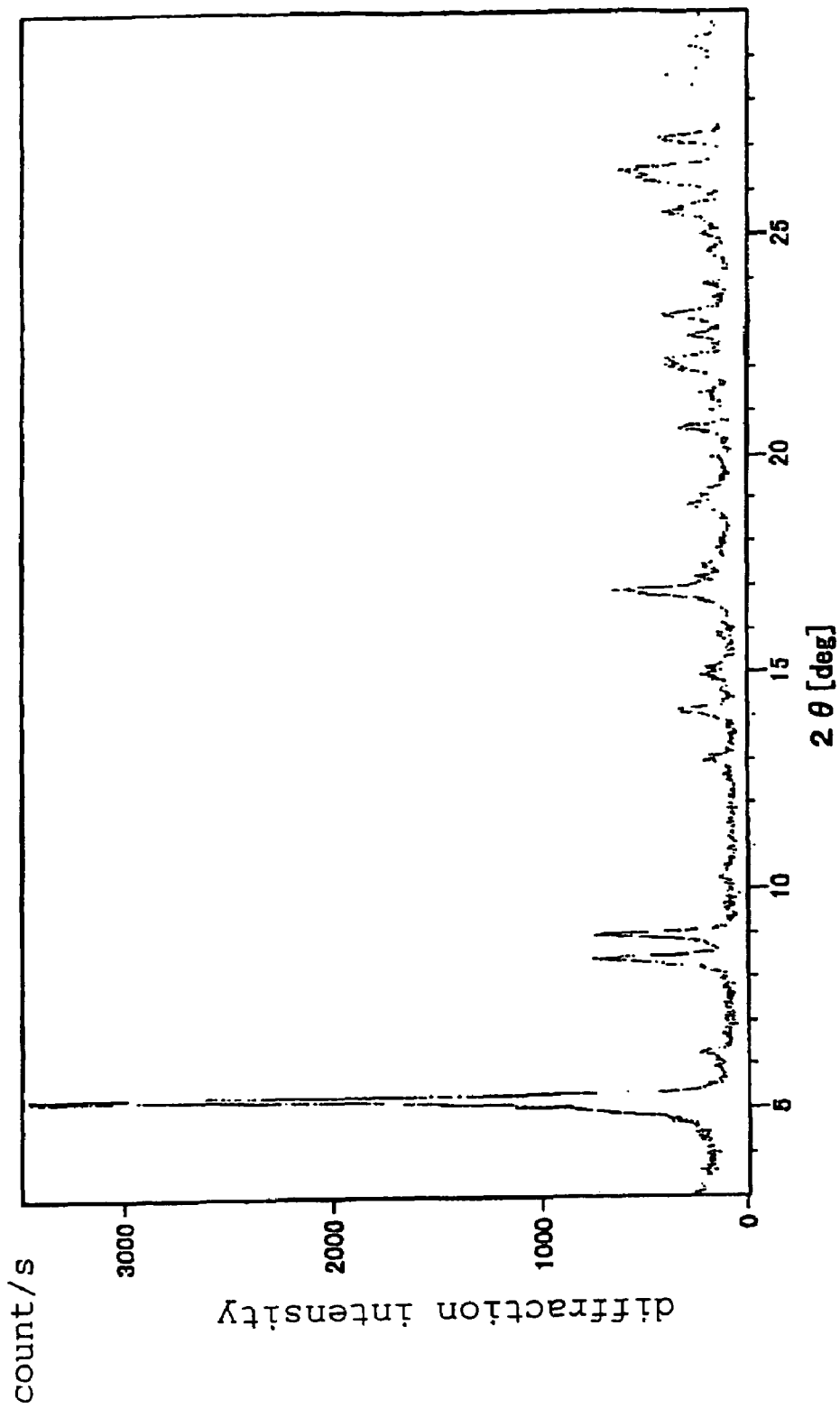
FIG. 1 is a powder X-ray diffractogram of the wet crystals of the (2R,4R)-monatin potassium salt of Example 1, wherein the vertical axis shows the diffraction intensity and the transverse axis shows the diffraction angle 2θ (degrees) (same for the following powder X-ray diffractograms)
Figure 2:
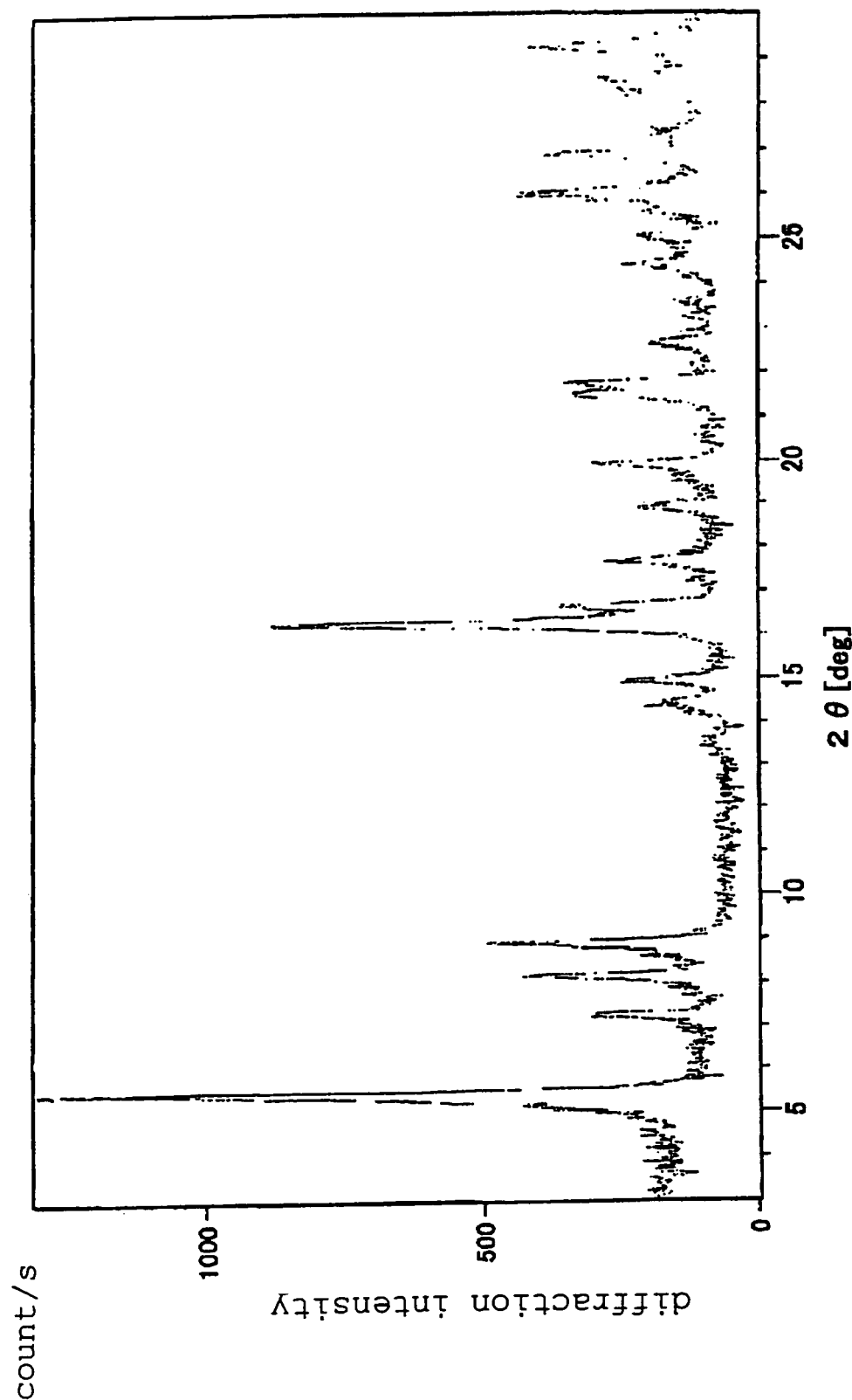
FIG. 2 is a powder X-ray diffractogram of the dry crystals of the (2R,4R)-monatin potassium salt of Example 1.
Figure 3:
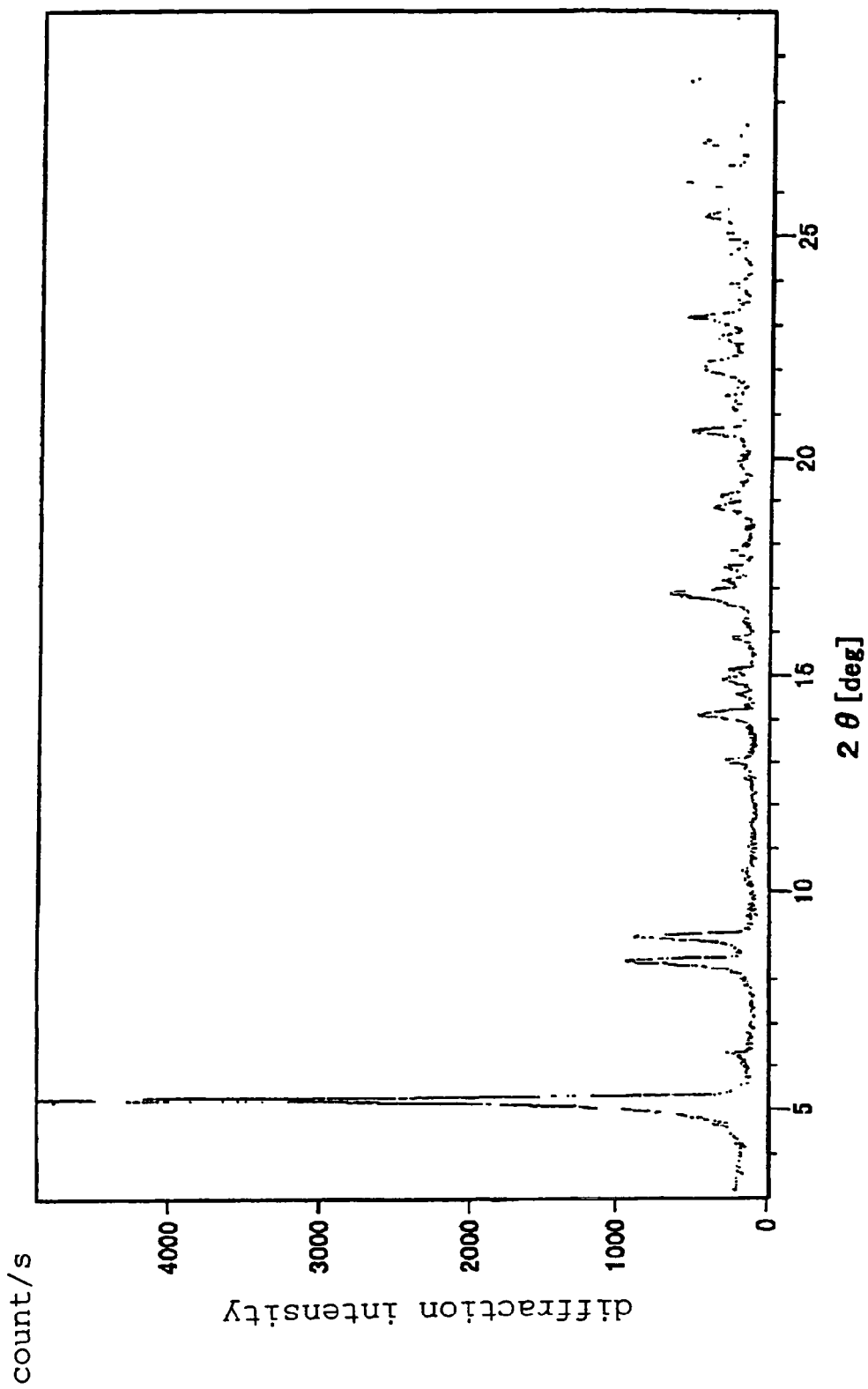
FIG. 3 is a powder X-ray diffractogram of the wet crystals of the (2R,4R)-monatin potassium salt of Example 2.
Figure 4:
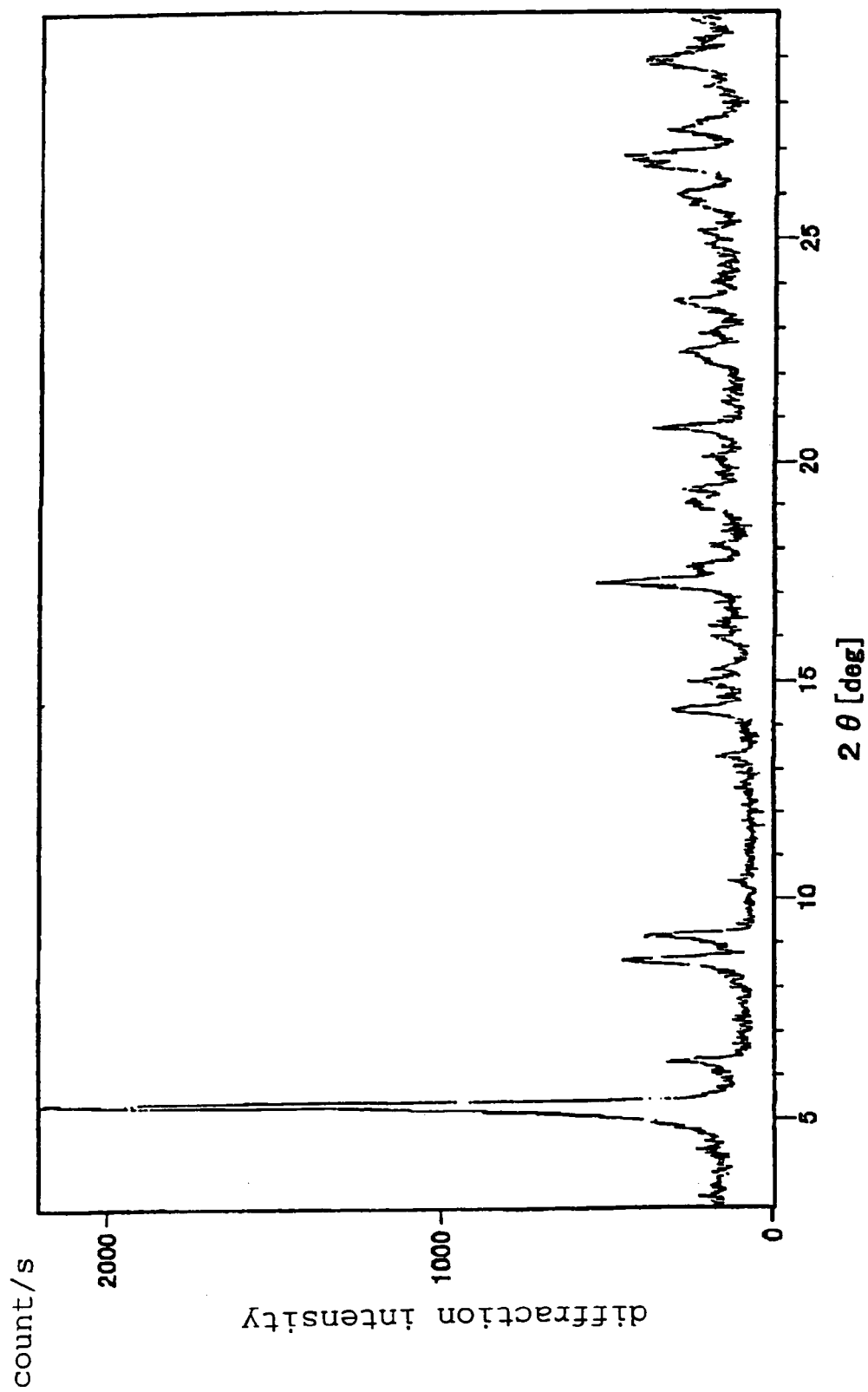
FIG. 4 is a powder X-ray diffractogram of the wet crystals of the (2R,4R)-monatin potassium salt of Example 3.
Figure 5:
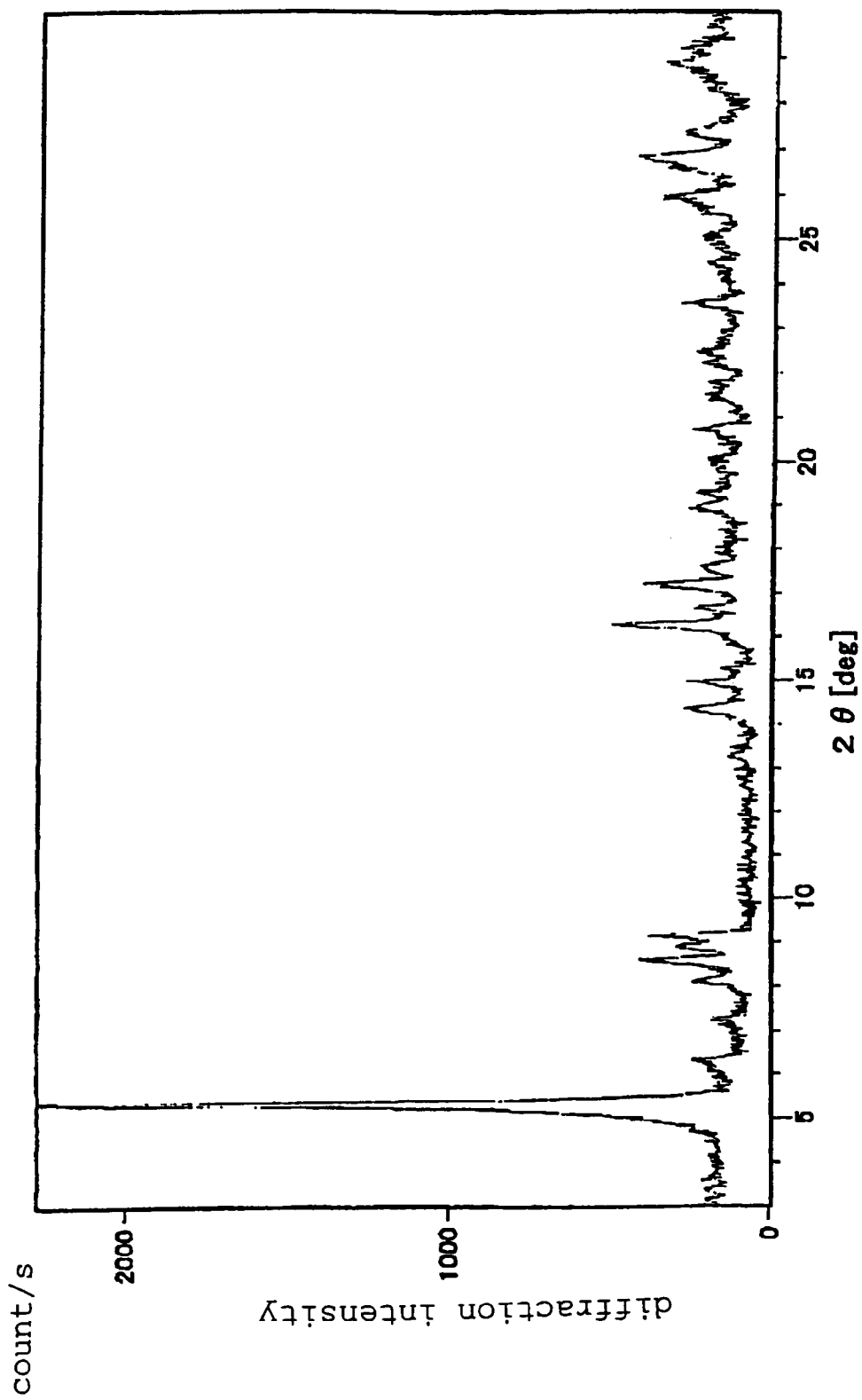
FIG. 5 is a powder X-ray diffractogram of the dry crystals of the (2R,4R)-monatin potassium salt of Example 3.
Figure 6:
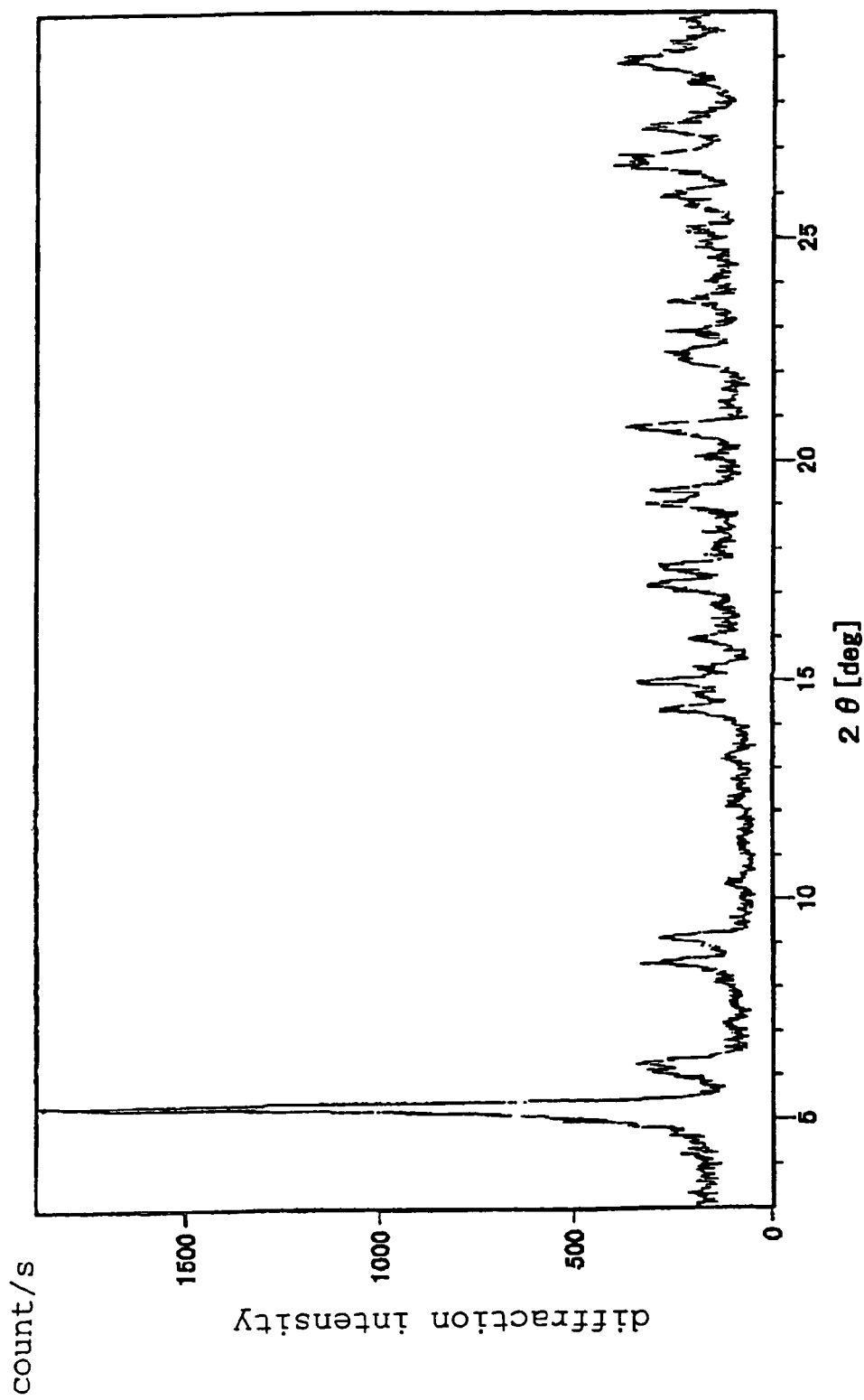
FIG. 6 is a powder X-ray diffractogram of the wet crystals of the (2R,4R)-monatin potassium salt of Example 4.
Figure 7:
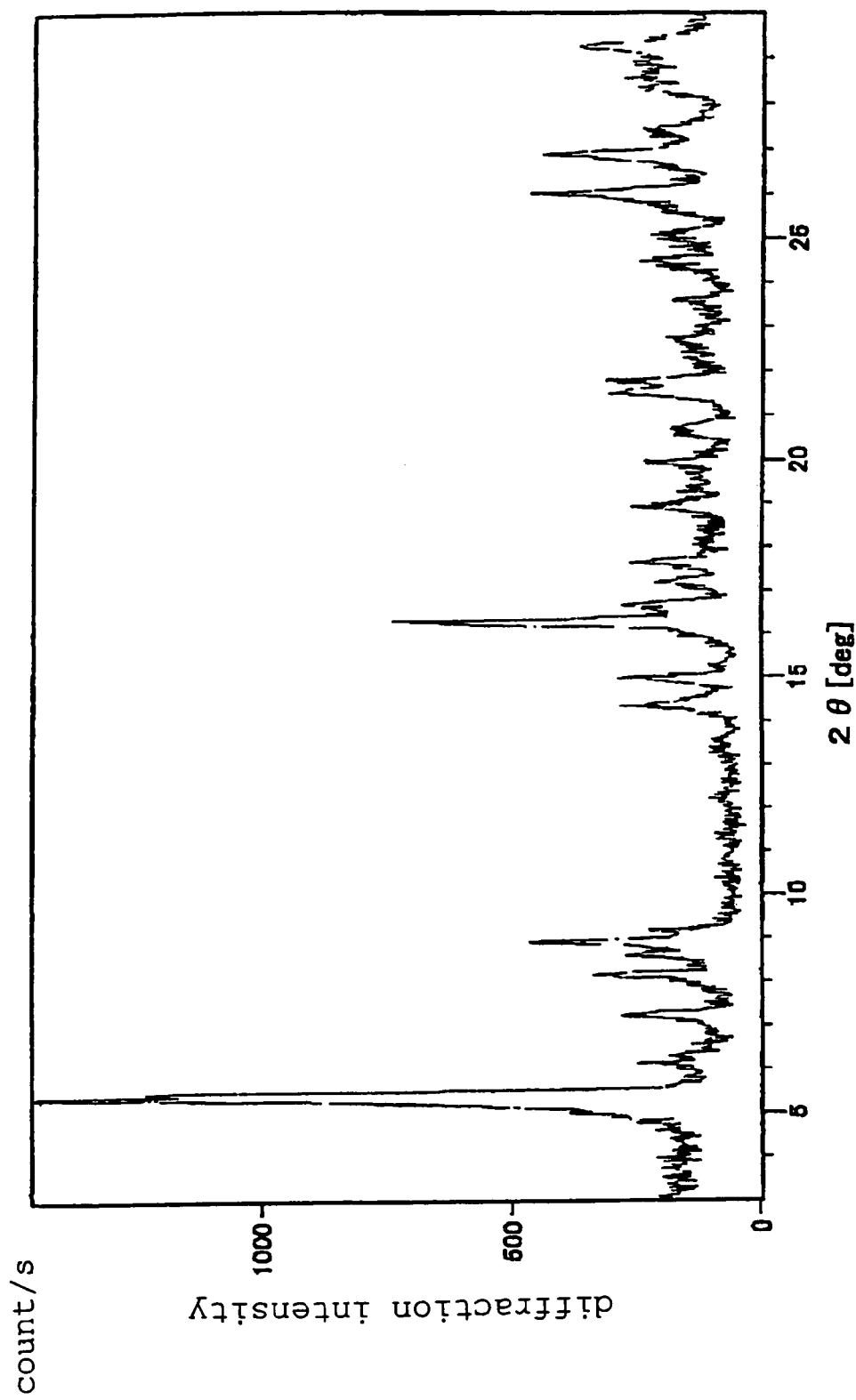
FIG. 7 is a powder X-ray diffractogram of the dry crystals of the (2R,4R)-monatin potassium salt of Example 4.
Figure 8:
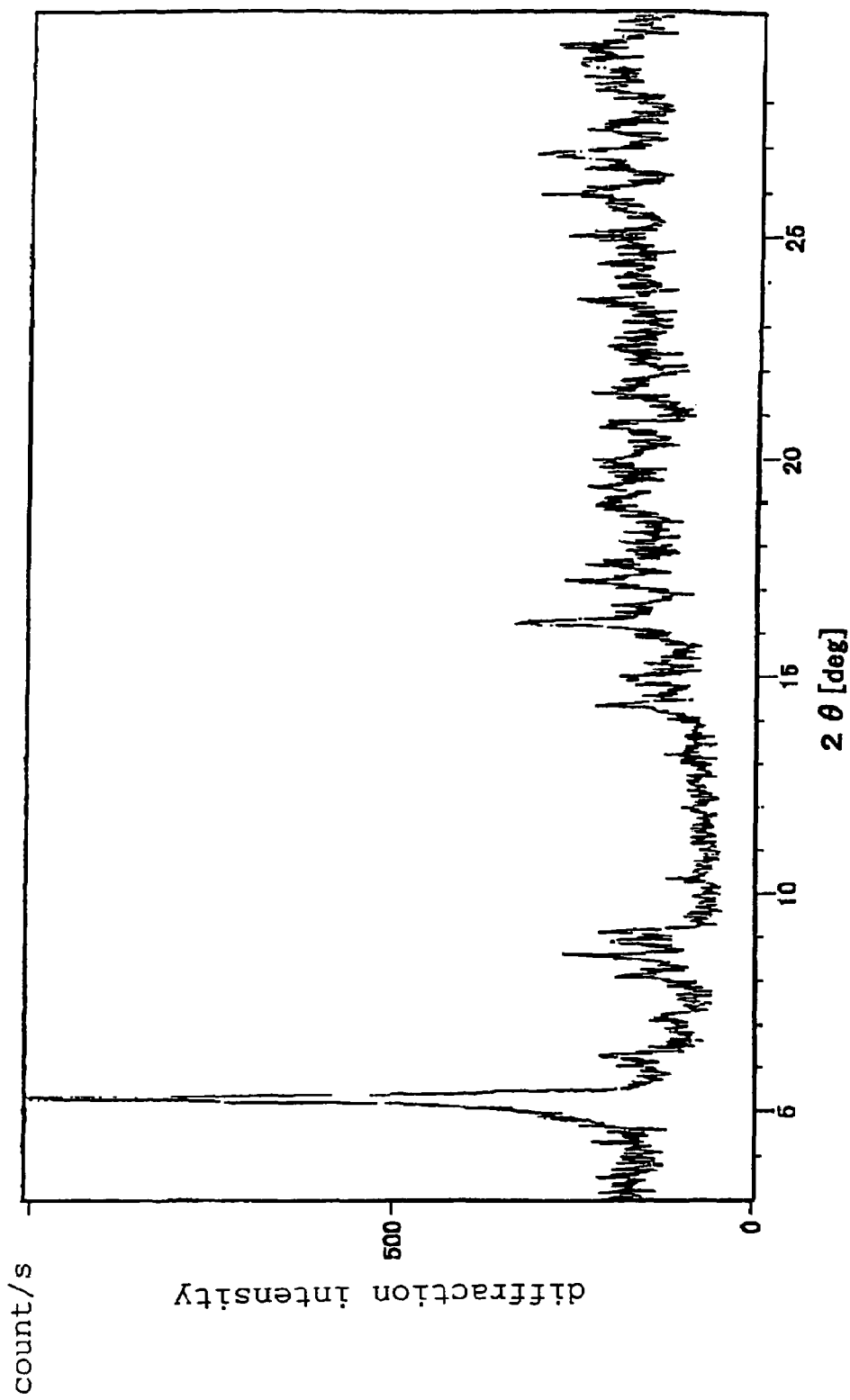
FIG. 8 is a powder X-ray diffractogram of the wet crystals of the (2R,4R)-monatin potassium salt of Example 5.
Figure 9:
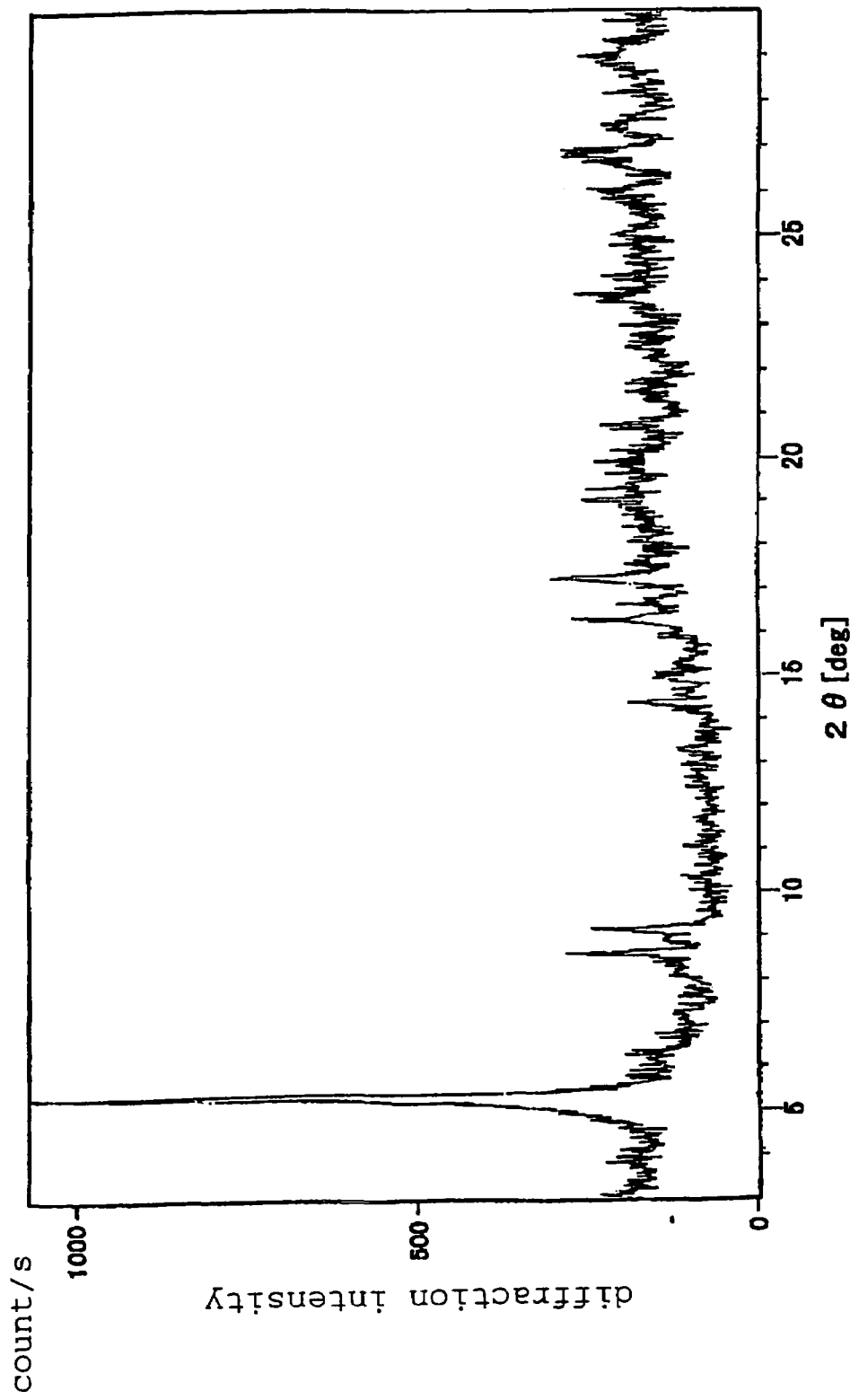
FIG. 9 is a powder X-ray diffractogram of the dry crystals of the (2R,4R)-monatin potassium salt of Example 5.
Figure 10:
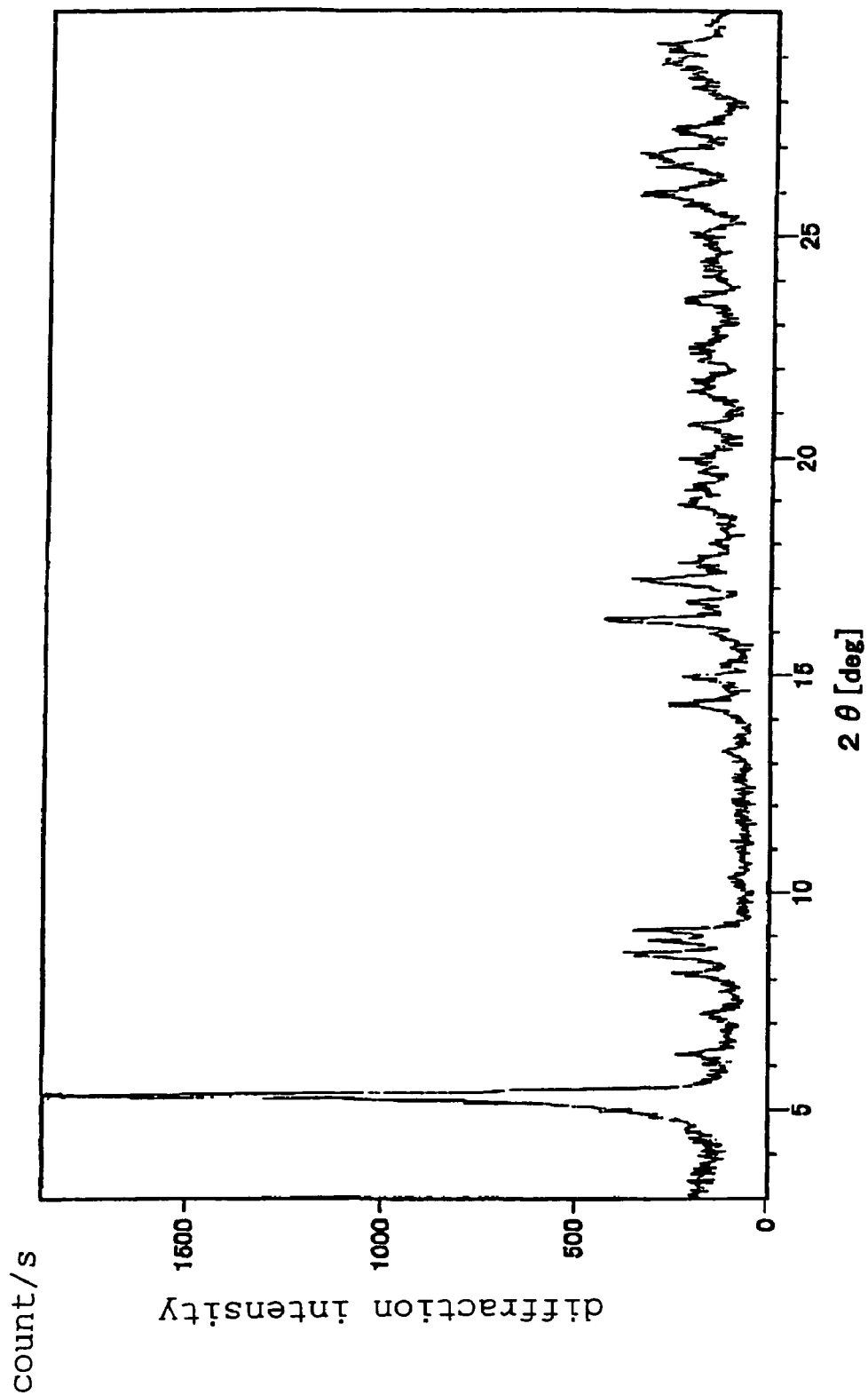
FIG. 10 is a powder X-ray diffractogram of the dry crystals of the (2R,4R)-monatin potassium salt of Example 7.
Figure 11:
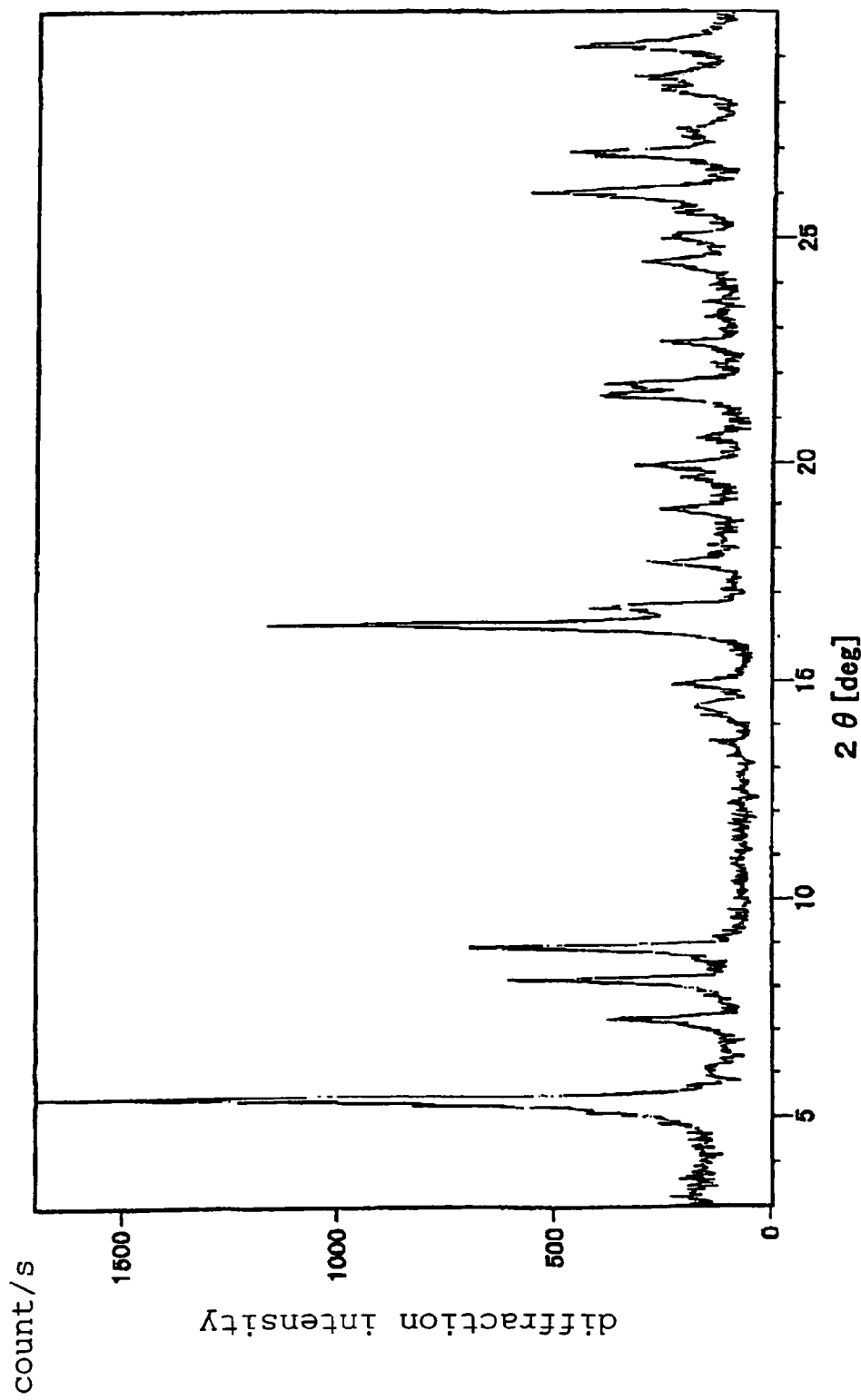
FIG. 11 is a powder X-ray diffractogram of the dry crystals of the (2R,4R)-monatin potassium salt of Example 8.
Figure 12:
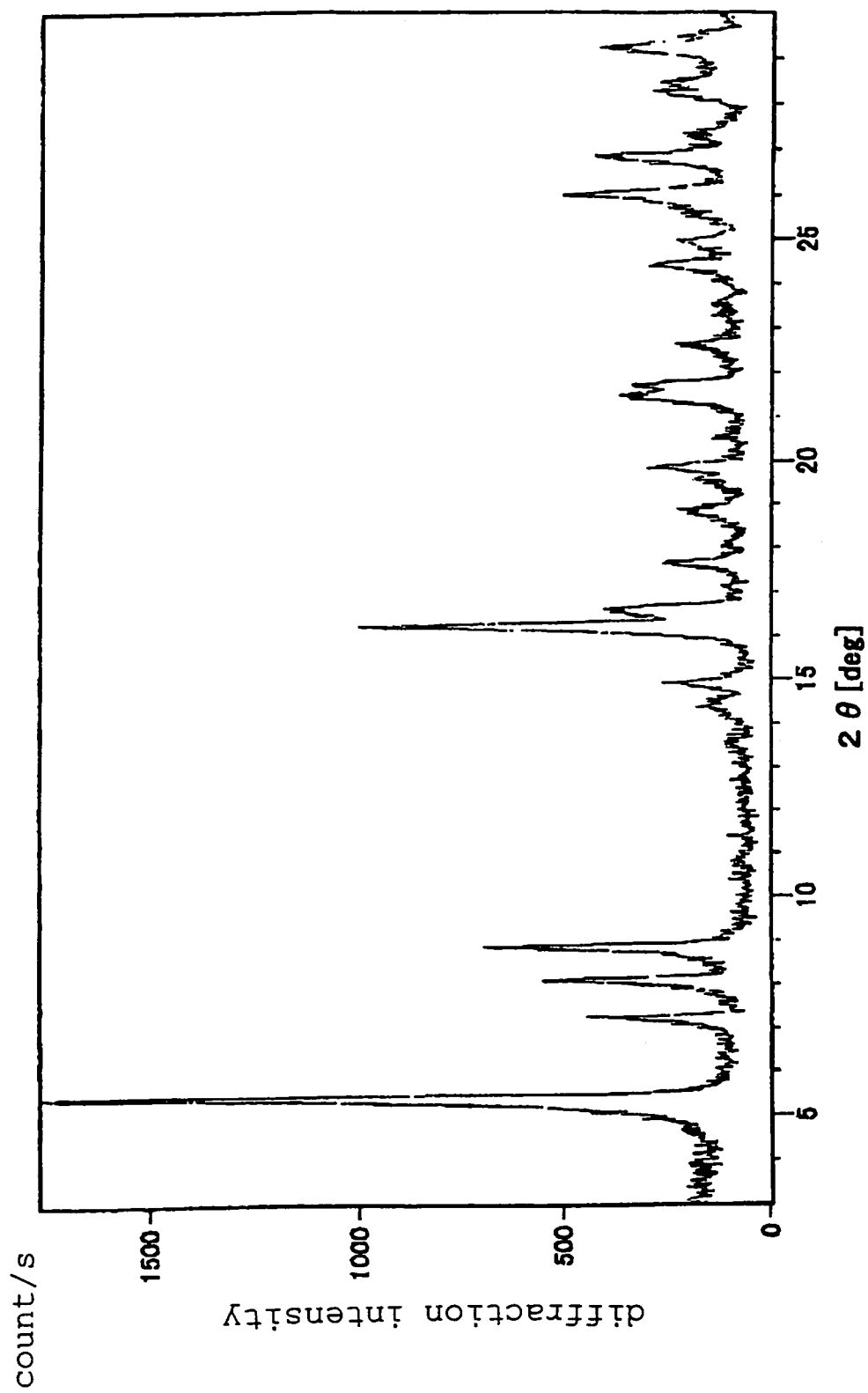
FIG. 12 is a powder X-ray diffractogram of the dry crystals of the (2R,4R)-monatin potassium salt of Example 9.
Figure 13:
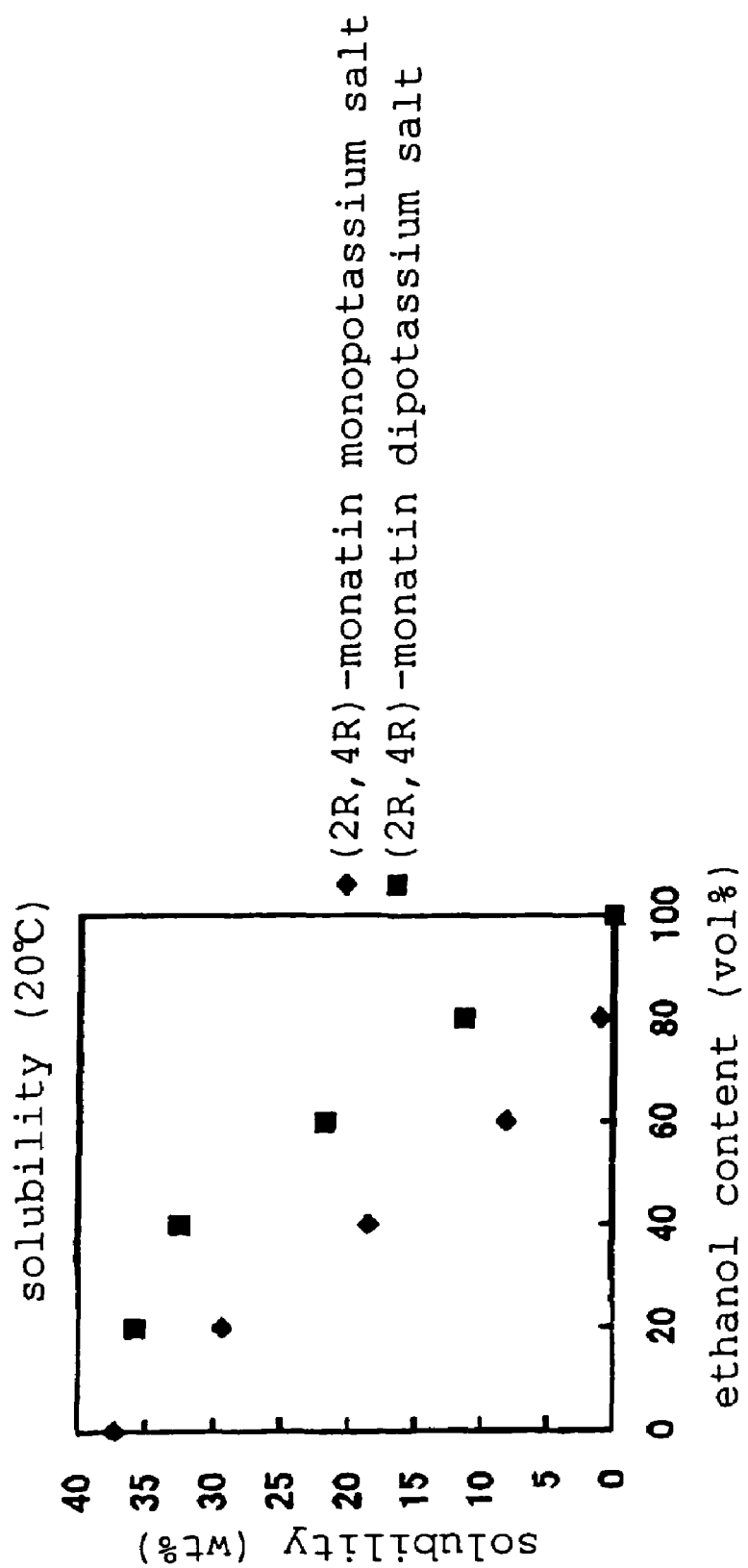
FIG. 13 is a graph reflecting the solubility values of Table 4.

The crystals of (2R,4R)-monatin potassium salt of the present invention are crystals of the potassium salt of (2R, 4R)-monatin, which is represented by the formula:

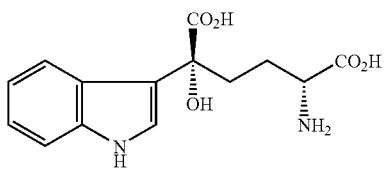

and show an X-ray powder diffraction pattern having characteristic peaks at diffraction angles 2θ of around 5.5°, 7.2°, 8.1°, 8.9°, and 16.3°, by powder X-ray diffraction (Cu—Kα radiation). The values of diffraction angle (2θ) in the powder X-ray analysis spectrum can have a measurement error of about ±0.2 degree. It is clear that the homology of the crystal form is not denied even if in the presence of such error.

The crystals of the (2R,4R)-monatin potassium salt of the present invention are crystals of a salt of (2R,4R)-monatin added with potassium. The amount of potassium to be added to 1 mol of (2R,4R)-monatin is preferably 1.2 to 2 mol, more preferably 1.8 to 2.0 mol. In other words, the crystals of the present invention preferably contain potassium in an amount of 1.2 to 2 moles, more preferably 1.8 to 2.0 moles, per mole of (2R,4R)-monatin.

The crystals of the (2R,4R)-monatin potassium salt of the present invention are generally hydrate crystals. In this case, the amount of water molecules hydrated per 1 mole of (2R, 4R)-monatin is preferably about 0.9 to 1.7 moles. Other solvents such as ethanol etc. may be added to the crystals of the present invention at an optional ratio as long as the effect of the present invention can be afforded and use as a sweetener is not impaired.

The crystals of (2R,4R)-monatin potassium salt of the present invention are preferably used as a sweetener. By adding other optional components such as carrier, extender, additive, flavoring and the like, a sweetener composition can be provided. The sweetener composition of the present invention may contain other sweeteners such as saccharides (e.g., sucrose, invert sugar, isomerized sugar, glucose, fructose, lactose, maltose, trehalose, xylose, etc.), sugar alcohols (e.g., multitol, sorbitol, mannitol, erythritol, xylitol, lactitol, etc.), oligosaccharides, dietary fiber, aspartame, saccharin, acesulfame K, sucralose, and the like.

The crystals of the present invention are preferably used in a sweetener composition. More particularly, the sweetener composition may be a freeze dried product, or a mixed ground product in which the crystals of the present invention are granulated, where necessary, according to a method known to those of ordinary skill in the art such as dry granulation, wet granulation, and the like to give granules.

The crystals and sweetener compositions of the present invention can be used for various foods such as powdered juices, powdered cocoa, instant coffee, chocolate, chewing gum, health foods, bread, cake, and the like, and various beverages such as coffee beverages, vegetable juice beverages, Japan tea, Chinese tea, tea, milk beverages, soup beverages, carbonated beverages, sweet beverages, juice beverages, alcohol beverages, and the like. In addition, crystals and sweetener compositions of the present invention can be used for various products that require a sweet taste such as toothpaste powders, pharmaceutical products and the like, and the like.

The crystals of the (2R,4R)-monatin potassium salt of the present invention can be produced from a (2R,4R)-monatin monopotassium salt. The monopotassium salt can be produced according to, for example, the description of the aforementioned K. Nakamura et al., *Organic Letters*, vol. 2, pp. 2967-2970 (2000) and WO03/045914.

For example, monatin is synthesized according to a method described in such known references, adsorbed onto a cation exchange resin (H+ type), eluted with 3% aqueous ammonia and purified by freeze-drying, whereby an ammonium salt of (2S)-monatin (a mixture of (2S,4S)-monatin and (2S,4R)-monatin) and an ammonium salt of (2R)-monatin (a mixture of (2R,4S)-monatin and (2R,4R)-monatin) can be obtained. By reversed phase HPLC, moreover, (2R,4R)-monatin can be separated in the form of an ammonium salt. Then, for example, according to a method described in WO03/045914, the ammonium salt of (2R,4R)-monatin is dissolved in water, and the obtained aqueous solution is passed through a column packed with a cation exchange resin, whereby the ammonium ion can be converted to a potassium ion. The solution eluted from the column is concentrated, heated to 60° C., and ethanol is added. The mixture is then cooled to 10° C. at a rate of 5° C./hour and stirred overnight at 10° C. As a result, crystals are precipitated in the liquid. The obtained crystals are recovered and dried in a vacuum dryer to give crystals of (2R,4R)-monatin monopotassium salt.

The crystals of (2R,4R)-monatin potassium salt of the present invention can be obtained by dispersing crystals of (2R,4R)-monatin monopotassium salt in a solvent, preferably in ethanol (or aqueous ethanol solution), adding an aqueous ethanol solution containing a potassium compound, preferably potassium hydroxide, to dissolve the crystal, and cooling the solution to allow crystal precipitation. The volume ratio of ethanol/water in the system is preferably not less than 10/1, more preferably not less than 20/1, further preferably not less than 40/1.

Other features of the invention will become apparent in the course of the following descriptions of exemplary embodiments which are given for illustration of the invention and are not intended to be limiting thereof.

EXAMPLES

In Examples and Comparative Examples, the (2R,4R)-monatin potassium salt of the present invention is conveniently referred to as the "(2R,4R)-monatin dipotassium salt."

The measurement of powder X-ray diffraction with Cu—Kα radiation was performed using an X-ray diffractometer PW3050 manufactured by Spectris Company using the following conditions of tube: Cu; tube current: 30 mA; tube voltage: 40 kV; sampling width: 0.020°; scan speed: 3°/minute; wavelength: 1.54056 Å; range of measured diffraction angles (2θ): 3 to 30°.

The molar ratio of (2R,4R)-monatin to potassium was determined by measuring the potassium ion concentration in a solution of the crystal of the (2R,4R)-monatin potassium salt having a given concentration, under the following conditions.

Cation measurement column: Shodex IC YK-421 manufactured by Showa Denko KK, inner diameter 4.6 mm, length 125 mm;

Eluent: 4 mM phosphoric acid+5 mM 18-Crown-6;

Column temperature: 40° C.; and

Flow rate: 0.6 ml/minute.

The molar ratio of (2R,4R)-monatin to ethanol was determined by measuring the NMR spectrum of a solution of the crystal of (2R,4R)-monatin potassium salt having a given concentration, under the following conditions, and calculating the integration ratio of (2R,4R)-monatin and ethanol from the obtained spectrum:

Apparatus: AVANCE400 manufactured by Bruker $^1$H; 400 MHz;
Solvent: heavy water;
Temperature: room temperature;
Concentration: about 7 wt %; and
Calculation method: The molar ratio was calculated from the ratio of the total (excluding active protons) of the proton integration value of (2R,4R)-monatin and the total (excluding active protons) of the proton integration value of ethanol.

The molar ratio of (2R,4R)-monatin to water was determined based on the concentration ratio obtained by measuring the water concentration of a solution of the crystal of (2R,4R)-monatin potassium salt having a given concentration, by the Karl Fischer's method under the following conditions:

Apparatus: automatic moisture measurement apparatus AQV-2000 manufactured by HIRANUMA SANGYO Co., Ltd.;
Titrant: Hydranal-composite 5 (manufactured by Riedel-deHaën);
Solvent: methanol; and
Temperature: room temperature.

Example 1

(2R,4R)-Monatin monopotassium salt (1.00 g, 3.03 mmol) was dispersed in ethanol (11.97 ml), and 1N potassium hydroxide/ethanol solution (3.03 ml, 3.03 mmol) was added at room temperature to dissolve the (2R,4R)-monatin monopotassium salt. The solution was cooled in an ice-bath with stirring to allow precipitation of crystals. The obtained crystals were separated to give wet crystals. The powder X-ray diffraction pattern of the wet crystals showed characteristic peaks at 5.3°, 8.5°, 9.1°, 14.3°, 17.1°, and 20.1°. The wet crystals were dried at 40° C. under reduced pressure to give dry crystals. The powder X-ray diffraction pattern (Cu Kα radiation, hereinafter the same) of the dry crystals showed characteristic peaks at 5.5°, 7.2°, 8.1°, 8.9°, and 16.3°.

Example 2

(2R,4R)-Monatin monopotassium salt (10.00 g, 30.3 mmol) was dispersed in ethanol (170 ml), and 1N potassium hydroxide/ethanol solution (30.27 ml, 30.3 mmol) was added at 20° C. to dissolve the (2R,4R)-monatin monopotassium salt, and the solution was stirred overnight. After cooling to 10° C., the crystals were separated and washed with ethanol (10 ml) to give wet crystals (16.05 g). The powder X-ray diffraction pattern of the wet crystals showed characteristic peaks at 5.3°, 8.5°, 9.1°, 14.3°, 17.1°, and 20.1°.

Example 3

(2R,4R)-Monatin monopotassium salt (0.50 g, 1.51 mmol) was dispersed in ethanol (9.885 ml), and 50 wt % aqueous potassium hydroxide solution (0.17 g, 1.51 mmol) was added at room temperature to dissolve the (2R,4R)-monatin monopotassium salt. The solution was cooled in an ice-bath with stirring to allow precipitation of crystals. The crystals were separated to give wet crystals (0.42 g). The powder X-ray diffraction pattern of the wet crystals showed characteristic peaks at 5.3°, 8.5°, 9.1°, 14.3°, 17.1°, and 20.1°.

Example 4

Wet crystals (0.64 g) were obtained in the same manner as in Example 3 except that ethanol (9.750 ml) and water (0.135 ml) were used instead of ethanol (9.885 ml). The powder X-ray diffraction pattern of the wet crystals showed characteristic peaks at 5.3°, 8.5°, 9.1°, 14.3°, 17.1°, and 20.1°.

Example 5

Wet crystals (0.17 g) were obtained in the same manner as in Example 3 except that ethanol (9.500 ml) and water (0.385 ml) were used instead of ethanol (9.885 ml). The powder X-ray diffraction pattern of the wet crystals showed characteristic peaks at 5.3°, 8.5°, 9.1°, 14.3°, 17.1°, and 20.1°.

Comparative Example 1

(2R,4R)-Monatin monopotassium salt (1.00 g, 3.03 mmol) was dispersed in ethanol (8.94 ml), and 1N potassium hydroxide/ethanol solution (6.06 ml, 6.06 mmol) was added at room temperature to dissolve the (2R,4R)-monatin monopotassium salt. The solution was cooled in an ice-bath with stirring, but crystals were not obtained.

Comparative Example 2

(2R,4R)-Monatin monopotassium salt (1.00 g, 3.03 mmol) was dispersed in ethanol (5.91 ml), and 1N potassium hydroxide/ethanol solution (9.09 ml, 9.09 mmol) was added at room temperature to dissolve the (2R,4R)-monatin monopotassium salt. The solution was cooled in an ice-bath with stirring, but crystals were not obtained.

Example 6

(2R,4R)-Monatin monopotassium salt (1.00 g, 3.03 mmol) was dispersed in ethanol (16.5 ml), and 1N potassium hydroxide/ethanol solution (1.5 ml, 1.5 mmol) was added at room temperature to give a slurry. The slurry was cooled in an ice-bath with stirring to allow precipitation of crystals. The crystals were separated and dried at 40° C. under reduced pressure. The powder X-ray diffraction pattern of the obtained dry crystals revealed that the obtained crystals were a mixture of monopotassium salt and dipotassium salt of (2R,4R)-monatin.

Comparative Example 3

(2R,4R)-Monatin monopotassium salt (1.00 g, 3.03 mmol) was dispersed in ethanol (13.5 ml), and 1N potassium hydroxide/ethanol solution (4.5 ml, 4.5 mmol) was added at room temperature to dissolve the (2R,4R)-monatin monopotassium salt. The solution was cooled in an ice-bath with stirring, but crystals were not obtained.

Comparative Example 4

(2R,4R)-Monatin monopotassium salt (0.50 g, 1.51 mmol) was dispersed in ethanol (9.0 ml) and water (0.885 ml), and 50 wt % aqueous potassium hydroxide solution (0.17 g, 1.51 mmol) was added at room temperature to dissolve the (2R,4R)-monatin monopotassium salt. The solution was cooled in an ice-bath with stirring, but crystals were not obtained.

Comparative Example 5

(2R,4R)-Monatin monopotassium salt (1.00 g, 3.03 mmol) was dispersed in ethanol (6.97 ml) and water (2 ml), and 1N potassium hydroxide/ethanol solution (3.03 ml, 3.03 mmol) was added at room temperature to dissolve the (2R,4R)- monatin monopotassium salt. The solution was cooled in an ice-bath with stirring, but crystals were not obtained.

Comparative Example 6

(2R,4R)-Monatin monopotassium salt (1.00 g, 3.03 mmol) was dispersed in ethanol (3.94 ml) and water (2 ml), and 1N potassium hydroxide/ethanol solution (6.06 ml, 6.06 mmol) was added at room temperature to dissolve the (2R,4R)-monatin monopotassium salt. The solution was cooled in an ice-bath with stirring, but crystals were not obtained.

Comparative Example 7

(2R,4R)-Monatin monopotassium salt (1.00 g, 3.03 mmol) was dispersed in ethanol (0.91 ml) and water (2 ml), and 1N potassium hydroxide/ethanol solution (9.09 ml, 9.09 mmol) was added at room temperature to dissolve the (2R,4R)-monatin monopotassium salt. The solution was cooled in an ice-bath with stirring, but crystals were not obtained.

The amount of potassium added, solvent, crystal precipitation concentration, and molar ratios of potassium, ethanol, and water relative to (2R,4R)-monatin in Examples 1-6 and Comparative Examples 1-7 are shown in Table 1 below.

TABLE 1

| | amount of potassium added | solvent | crystal precipitation concentration (g/dl) | molar ratio relative to (2R,4R)-monatin | | |
|---|---|---|---|---|---|---|
| | | | | potassium | ethanol | water |
| Ex. 1 | 1.0 | ethanol | 6.7 | 1.8 | 0.04 | 1.1 |
| Ex. 2 | 1.0 | ethanol | 6.7 | 1.8 | — | — |
| Ex. 3 | 1.0 | ethanol/water = 116/1 | 5.0 | 1.8 | 0.27 | 1.1 |
| Ex. 4 | 1.0 | ethanol/water = 44/1 | 5.0 | 1.8 | 0.23 | 1.1 |
| Ex. 5 | 1.0 | ethanol/water = 20/1 | 5.0 | 1.9 | 0.14 | 1.5 |
| Ex. 6 | 0.5 | ethanol | 5.6 | 1.7 | 0.02 | 1.2 |
| Comp. Ex. 1 | 2.0 | ethanol | 6.7 | — | — | — |
| Comp. Ex. 2 | 3.0 | ethanol | 6.7 | — | — | — |
| Comp. Ex. 3 | 1.5 | ethanol | 5.6 | — | — | — |
| Comp. Ex. 4 | 1.0 | ethanol/water = 9/1 | 5.0 | — | — | — |
| Comp. Ex. 5 | 1.0 | ethanol/water = 5/1 | 8.3 | — | — | — |
| Comp. Ex. 6 | 2.0 | ethanol/water = 5/1 | 8.3 | — | — | — |
| Comp. Ex. 7 | 3.0 | ethanol/water = 5/1 | 8.3 | — | — | — |

* In Table 1, the "amount of potassium added" is shown as a molar ratio relative to the moles of (2R,4R)-monatin.
* In Table 1, the "solvent" refers to the solvent after addition of potassium hydroxide solution, and the ratio when a mixed solvent was used is shown as a volume ratio.
* In Table 1, the "molar ratio" is a value from the measurement of dry crystals obtained by drying the wet crystals of each (Comparative) Example.
* The molar ratio of ethanol and water was not measured for Example 2.

Example 7

The wet crystals (0.473 g) of (2R,4R)-monatin dipotassium salt obtained in Example 2 were placed in a dish and left standing overnight at 40° C. As a result, 0.23 g of the crystals were obtained. The powder X-ray diffraction pattern of the wet crystals showed characteristic peaks at 5.5°, 7.2°, 8.1°, 8.9°, and 16.3°.

Example 8

The wet crystals (0.483 g) of (2R,4R)-monatin dipotassium salt obtained in Example 2 were placed in a dish and left standing overnight at 80° C. As a result, 0.22 g of the crystals were obtained. The powder X-ray diffraction pattern of the wet crystals showed characteristic peaks at 5.5°, 7.2°, 8.1°, 8.9°, and 16.3°.

Example 9

2R,4R)-Monatin monopotassium salt (0.50 g 1.51 mmol) was dispersed in ethanol (13.6 ml), and 50 wt % aqueous potassium hydroxide solution (0.17 g, 1.51 mmol) was added at 10° C. The mixture was stirred at 10° C. for 17.5 hours to allow precipitation of crystals. The crystals were separated to give wet crystals (1.31 g). The wet crystals were dried under vacuum at 40° C. for about 2 hr to give crystals (0.52 g). The powder X-ray diffraction pattern of the crystals showed characteristic peaks at 5.5°, 7.2°, 8.1°, 8.9°, and 16.3°. The molar ratio of potassium relative to the moles of (2R,4R)-monatin was 1.4, the molar ratio of ethanol relative to the moles of (2R,4R)-monatin was 0.63, and the molar ratio of water relative to the moles of (2R,4R)-monatin was 0.87.

Coloring Test:

The crystals of the (2R,4R)-monatin dipotassium salt obtained in Example 9, (2R,4R)-monatin, and crystals of the (2R,4R)-monatin monopotassium salt produced according to the production method described in the aforementioned WO03/045914 were subjected to a coloring test. The results are shown in Table 2.

Measurement Method of Coloring Test:
- Measurement device: CARY 50 UV-VIS spectrophotometer manufactured by Varian Technologies Japan Limited;
- Concentration: 1 g/dl;
- Solvent: $H_2O$;
- Temperature: room temperature;
- Measurement wavelength: 490 nm; and
- Measurement interval: 30 minutes.

TABLE 2

| sample time (hour) | crystal of (2R,4R)-monatin monopotassium salt | (2R,4R)-monatin | crystal of (2R,4R)-monatin dipotassium salt |
|---|---|---|---|
| | transmittance (%) | | |
| 0.0 | 100.02 | 97.38 | 99.63 |
| 2.0 | 99.75 | 94.47 | 99.60 |
| 4.0 | 99.28 | 90.77 | 99.51 |
| 6.0 | 98.42 | 87.30 | 99.43 |
| 8.0 | 97.98 | 85.02 | 99.44 |
| 10.0 | 96.86 | 83.71 | 99.44 |
| 12.0 | 95.61 | 82.71 | 99.41 |
| 14.0 | 94.35 | 81.85 | 99.42 |
| 16.0 | 92.97 | 81.14 | 99.39 |
| 18.0 | 91.49 | 80.66 | 99.35 |
| 20.0 | 90.05 | 80.38 | 99.39 |
| 22.0 | 88.75 | 80.21 | 99.38 |

From Table 2, it is clear that the crystals of the (2R,4R)-monatin dipotassium salt of the present invention are superior to crystals of (2R,4R)-monatin and crystals of the (2R,4R)-monatin monopotassium salt in regard to color stability.

Preservation Stability Test:

The crystals of the (2R,4R)-monatin dipotassium salt obtained in Example 1 and Example 9, and crystals of the (2R,4R)-monatin monopotassium salt produced according to the production method described in the aforementioned WO03/045914 were subjected to a preservation stability test. Each sample (50 mg) was placed in a 4 ml vial (with screw cap) and stored at 60° C. and room temperature for 1 week.

A chromatogram for each sample was measured by HPLC, and the HPLC quantitation value of the 60° C. preservation sample, when that of the room temperature preservation sample was 100%, was shown as a weight change. In addition, an HPLC chromatogram of each sample was measured and the ratio of the area value of (2R,4R)-monatin relative to the total area value of the entire peaks detected (detection wavelength: 210 nm) in the 60° C. preservation sample was expressed as the area %. The results are shown in Table 3.

TABLE 3

| | sample | weight change (%) | area % |
|---|---|---|---|
| | (2R,4R)-monatin monopotassium salt | 100 | 99.8 |
| Example 9 | (2R,4R)-monatin dipotassium salt | 103 | 99.6 |
| Example 1 | (2R,4R)-monatin dipotassium salt | 99 | 98.4 |

From Table 3, it is clear that the preservation stability of (2R,4R)-monatin dipotassium salt was almost of the same level as the (2R,4R)-monatin monopotassium salt.

Solubility Test:

The crystals of the (2R,4R)-monatin dipotassium salt obtained in Example 9 and crystals of the (2R,4R)-monatin monopotassium salt were tested for solubility using the following conditions"

Temperature: 20° C.; and

Solubility measurement method: Two test tubes for each of 0, 20, 40, 60, 80, 100% ethanol, which contained 2 ml thereof were prepared. The crystals of the (2R,4R)-monatin dipotassium salt and crystals of the (2R,4R)-monatin monopotassium salt were added thereto in an amount prohibiting complete dissolution. The test tubes were capped and stirred overnight. Then, the mixture was passed through a filter (0.45 μm) and the filtrate was analyzed. The results are shown in Table 4.

TABLE 4

| | | ethanol amount (vol %) | | | | | |
|---|---|---|---|---|---|---|---|
| | | 0 | 20 | 40 | 60 | 80 | 100 |
| solubility (wt %) | (2R,4R)-monatin monopotassium salt | 37.3 | 29.37 | 18.57 | 8.14 | 1.04 | 0.01 |
| | (2R,4R)-monatin dipotassium salt | — | 35.75 | 32.53 | 21.86 | 11.38 | 0.02 |

From Table 4, it is clear that the (2R,4R)-monatin dipotassium salt was superior to (2R,4R)-monatin monopotassium salt in regard to solubility.

INDUSTRIAL APPLICABILITY

The crystals of the (2R,4R)-monatin potassium salt of the present invention have a high sweetness, are superior in preservation stability, and superior to the crystals of the (2R,4R)-monatin monopotassium salt in regard to solubility and color stability. Therefore, the crystals of the present invention are extremely useful industrially as a sweetener or a component thereof, and as a novel sweet substance having superior properties as a sweetness imparting component for food, drink and the like, particularly in the field of foodstuffs.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A dipotassium salt of (2R,4R)-monatin.

2. A crystal of a (2R,4R)-monatin dipotassium salt according to claim 1, which exhibits an X-ray powder diffraction pattern having characteristic peaks at diffraction angles 2θ of 5.5°, 7.2°, 8.1°, 8.9° and 16.3°, by powder X-ray diffraction using Cu—Kα radiation.

3. The crystal of claim 2, which has a molar ratio of potassium to (2R,4R)-monatin within the range of 1.2 to 2.

4. The crystal of claim 2, which has a molar ratio of water to (2R,4R)-monatin within the range of 0.9 to 1.7.

5. A crystal of a (2R,4R)-monatin dipotassium salt according to claim 1, having a molar ratio of potassium to (2R,4R)-monatin within the range of 1.2 to 2.

6. The crystal of claim 5, which has a molar ratio of water to (2R,4R)-monatin within the range of 0.9 to 1.7.

7. A sweetener composition, comprising the dipotassium salt of (2R,4R)-monatin of claim 1.

8. The sweetener composition of claim 7, wherein said dipotassium salt of (2R,4R)-monatin potassium salt has a molar ratio of potassium to (2R,4R)-monatin within the range of 1.2 to 2.

9. The sweetener composition of claim 7, wherein said dipotassium salt of (2R,4R)-monatin potassium salt has a molar ratio of water to (2R,4R)-monatin within the range of 0.9 to 1.7.

10. The sweetener composition of claim 7, further comprising at least one ingredient selected from the group consisting of a carrier, extender, additive, flavoring and mixtures thereof.

11. The sweetener composition of claim 7, further comprising at least one ingredient selected from the group consisting of sucrose, invert sugar, isomerized sugar, glucose, fructose, lactose, maltose, trehalose, xylose, multitol, sorbitol, mannitol, erythritol, xylitol, lactitol, oligosaccharides, dietary fiber, aspartame, saccharin, acesulfame K, sucralose, and mixtures thereof.

12. A sweetener composition comprising the crystal of (2R,4R)-monatin dipotassium salt of claim 5.

13. The sweetener composition of claim 12, wherein said crystal of (2R,4R)-monatin dipotassium salt has a molar ratio of water to (2R,4R)-monatin within the range of 0.9 to 1.7.

14. The sweetener composition of claim 13, further comprising at least one ingredient selected from the group consisting of a carrier, extender, additive, flavoring and mixtures thereof.

15. The sweetener composition of claim 13, further comprising at least one ingredient selected from the group consisting of sucrose, invert sugar, isomerized sugar, glucose, fructose, lactose, maltose, trehalose, xylose, multitol, sorbitol, mannitol, erythritol, xylitol, lactitol, oligosaccharides, dietary fiber, aspartame, saccharin, acesulfame K, sucralose, and mixtures thereof.

16. A method of preparing crystals of a (2R,4R)-monatin dipotassium salt according to claim 1, comprising:
(a) dispersing crystals of (2R,4R)-monatin monopotassium salt in a solvent, preferably in ethanol or aqueous ethanol solution, to obtain a suspension;
(b) adding an aqueous ethanol solution containing a potassium compound, preferably potassium hydroxide, to said suspension to dissolve said crystals and obtain a solution; and
(c) cooling said solution to obtain said crystals of the (2R,4R)-monatin dipotassium salt.

17. The method of claim 16, wherein the volume ratio of ethanol/water in said solution is not less than 20/1.

18. The method of claim 16, wherein said crystals of the (2R,4R)-monatin dipotassium salt exhibit an X-ray powder diffraction pattern having characteristic peaks at diffraction angles 2θ of 5.5°, 7.2°, 8.1°, 8.9° and 16.3°, by powder X-ray diffraction using Cu—Kα radiation.

19. The method of claim 16, wherein said crystals of (2R,4R)-monatin dipotassium salt have a molar ratio of potassium to (2R,4R)-monatin within the range of 1.2 to 2.

20. The method of claim 16, wherein said crystals of (2R,4R)-monatin dipotassium salt have a molar ratio of water to (2R,4R)-monatin within the range of 0.9 to 1.7.

* * * * *